(12) United States Patent　　(10) Patent No.:　　US 11,234,644 B2
Kochura et al.　　　　　　　　　　(45) Date of Patent:　　Feb. 1, 2022

(54) MONITORING AND DETERMINING THE STATE OF HEALTH OF A USER

(71) Applicant: International Business Machines Corporation, Armonk, NY (US)

(72) Inventors: Nadiya Kochura, Bolton, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 271 days.

(21) Appl. No.: 15/844,957

(22) Filed: Dec. 18, 2017

(65) Prior Publication Data

US 2019/0074089 A1　　Mar. 7, 2019

Related U.S. Application Data

(63) Continuation of application No. 15/695,067, filed on Sep. 5, 2017.

(51) Int. Cl.
*G16H 50/30*　　(2018.01)
*A61B 5/00*　　(2006.01)
(Continued)

(52) U.S. Cl.
CPC .......... *A61B 5/6822* (2013.01); *A61B 5/4205* (2013.01); *A61B 5/747* (2013.01);
(Continued)

(58) Field of Classification Search
CPC ... G06F 19/3418; A61B 5/6822; A61B 5/747; A61B 5/4205; A61B 2562/0204;
(Continued)

(56) References Cited

U.S. PATENT DOCUMENTS 8,118,758 B2　　2/2012　Kandori et al.
9,198,613 B2　　12/2015　Oh
(Continued)

FOREIGN PATENT DOCUMENTS

CN　　103914732 B　　2/2017
EP　　2667777 A2　　12/2013
(Continued)

OTHER PUBLICATIONS

List of IBM Patents or Patent Applications Treated as Related, Appendix P, Filed Herewith, 2 pages.
(Continued)

*Primary Examiner* — John A Pauls
(74) *Attorney, Agent, or Firm* — Edward J. Wixted, III

(57) ABSTRACT

A method for identifying a change associated with a state of health of a user. In one embodiment, the method includes at least one computer processors receiving monitoring data associated with monitoring a user, where the monitoring data is generated by one or more sensors. The method further includes determining a state of health of the monitored user by analyzing the monitoring data utilizing one or more models. The method further includes determining a level of urgency based, at least in part, upon the determine state of health of the monitored user. The method further includes transmitting one or more respective notifications to one or more devices based, at least in part, on the determined state of health of the user and the corresponding level of level of urgency, and where a notification includes a determined state of health and the corresponding determined state of urgency associated with the monitored user.

11 Claims, 4 Drawing Sheets

(51) Int. Cl.
*G16H 50/20* (2018.01)
*G16H 50/50* (2018.01)
*G16H 20/60* (2018.01)
*G16H 40/67* (2018.01)
*G16H 10/60* (2018.01)
*G16H 15/00* (2018.01)

(52) U.S. Cl.
CPC ............ *G16H 10/60* (2018.01); *G16H 15/00* (2018.01); *G16H 20/60* (2018.01); *G16H 40/67* (2018.01); *G16H 50/20* (2018.01); *G16H 50/30* (2018.01); *G16H 50/50* (2018.01); *A61B 2505/07* (2013.01); *A61B 2505/09* (2013.01); *A61B 2562/0204* (2013.01)

(58) Field of Classification Search
CPC ............ A61B 2505/09; A61B 2505/07; G16H 15/00; G16H 10/60; G16H 50/20; G16H 50/30; G06Q 50/22–24
See application file for complete search history.

(56) References Cited

U.S. PATENT DOCUMENTS

| | | | |
|---|---|---|---|
| 9,198,621 B2 | 12/2015 | Fernstrom et al. | |
| 2008/0167675 A1 | 7/2008 | Hogosta et al. | |
| 2008/0242951 A1* | 10/2008 | Jung | A61B 5/411 600/300 |
| 2010/0228102 A1* | 9/2010 | Addison | A61B 5/0205 600/301 |
| 2010/0293005 A1* | 11/2010 | Glimp | G16H 40/67 705/2 |
| 2011/0125063 A1* | 5/2011 | Shalon | A61B 5/1112 600/590 |
| 2011/0160615 A1 | 6/2011 | Matsumura | |
| 2013/0310661 A1 | 11/2013 | Jedwab et al. | |
| 2014/0081578 A1 | 3/2014 | Connor | |
| 2014/0228714 A1 | 8/2014 | Chau et al. | |
| 2014/0236627 A1* | 8/2014 | Odessky | G16H 50/30 705/3 |
| 2014/0349256 A1 | 11/2014 | Connor | |
| 2015/0038805 A1 | 2/2015 | Bhargava | |
| 2015/0100344 A1* | 4/2015 | Chen | G06F 19/00 705/2 |
| 2015/0112150 A1 | 4/2015 | Bernhard | |
| 2015/0302150 A1* | 10/2015 | Mazar | G08B 21/0211 705/2 |
| 2016/0026767 A1 | 1/2016 | Sarrafzadeh et al. | |
| 2016/0073953 A1 | 3/2016 | Sazonov | |
| 2017/0027495 A1 | 2/2017 | Jedwab et al. | |
| 2017/0323064 A1* | 11/2017 | Bates | A61B 5/0002 |
| 2018/0184977 A1* | 7/2018 | Mias | A61B 5/0077 |
| 2018/0341747 A1* | 11/2018 | Bernard | A61B 5/0022 |

FOREIGN PATENT DOCUMENTS

| | | | | |
|---|---|---|---|---|
| JP | 2004110222 | * | 4/2004 | ............ G06F 17/60 |
| KR | 20080058337 A | * | 6/2008 | ............ A61B 5/0064 |
| WO | 2005117617 A1 | | 12/2005 | |
| WO | WO-2010104978 A2 | * | 9/2010 | ............ A61B 5/0002 |
| WO | 2014081401 A1 | | 5/2014 | |
| WO | 2014163784 A1 | | 10/2014 | |

OTHER PUBLICATIONS

Kochura, et al., "Monitoring and Determining the State of Health of a User", U.S. Appl. No. 15/695,067, filed Sep. 5, 2017.

Kurihara, et al., "Evaluation of Swallowing Function Using an Optical Sensor-based System for In-home Nursing", SICE-ICASE International Joint Conference 2006, Oct. 18-21, 2006 in Bexco, Busan, Korea, 4 pages.

Svensson P, Hartelius L., "Speech and Swallowing Symptoms Associated with Parkinson's Disease and Multiple Sclerosis: A Survey", Folia Phoniatr Logop, vol. 46, No. 1, 1994, Issue release date: 1994, Section title: Original Paper, 5 pages, <http://www.karger.com/Article/Abstract/266286>.

Wang et al., "Real-Time Hand-Tracking with a Color Glove", Printed Oct. 5, 2021, 8 pages.

* cited by examiner

MONITORING AND DETERMINING THE STATE OF HEALTH OF A USER

BACKGROUND OF THE INVENTION

The present invention relates generally to the field of medical data acquisition and analysis, and more particularly to monitoring and analyzing physiological information related to a user to identify potential medical issues.

There are a variety of methods, known in the art, for monitoring the mechanics of eating and swallowing (i.e., deglutition) of an individual with a medical condition. A set of sounds produced during eating and swallowing can be processed and analyzed to aid in diagnosing a state of health for some aspect of an individual. Similarly, there are mechanisms and models that can describe or analyze the biomechanics of the consumption of food and/or beverages based on various quantitative measures, such as temperature, consistency, quantity, etc. In addition, models associated with the consumption of food and/or beverages are further affected by non-quantitative parameters, such as taste, presentation (e.g., an appetizing appearance, and user likes/dislikes.

Individuals with known medical conditions may be advised by medical professionals to identify various actions associated with eating and/or drinking that can signal a negative health effect for the individual. Alternatively, medical professionals can request the individual to keep a personal journal and upon review of the personal journal the medical professionals may advise the individual of apparent changes that signal a worsening of the medical condition. In some instances, monitoring the eating and swallowing behaviors of an individual within a controlled setting, such as a hospital, an office of a doctor, a skilled nursing facility, or within a residence by a trained home healthcare worker provides one set of diagnostic information. In other instances, such controlled settings are less conducive to frequent monitoring of an individual, affects the quality of life of the individual, and may less accurately reflect the eating and swallowing behaviors of the individual.

SUMMARY

According to aspects of the present invention, there is a method, computer program product, and/or system for identifying a change associated with a state of health of a user. In an embodiment, the method includes receiving monitoring data associated with monitoring a user, where the monitoring data is generated by one or more sensors. The method further includes determining a state of health of the monitored user by analyzing the monitoring data utilizing one or more models. The method further includes determining a level of urgency based, at least in part, upon the determined state of health of the monitored user. The method further includes transmitting one or more respective notifications to one or more devices based, at least in part, on the determined state of health of the user and the corresponding level of urgency, where the one or more devices includes a device associated with the monitored user, and where a notification includes a determined state of health and the corresponding determined state of urgency associated with the monitored user.

DETAILED DESCRIPTION

Figure 1:
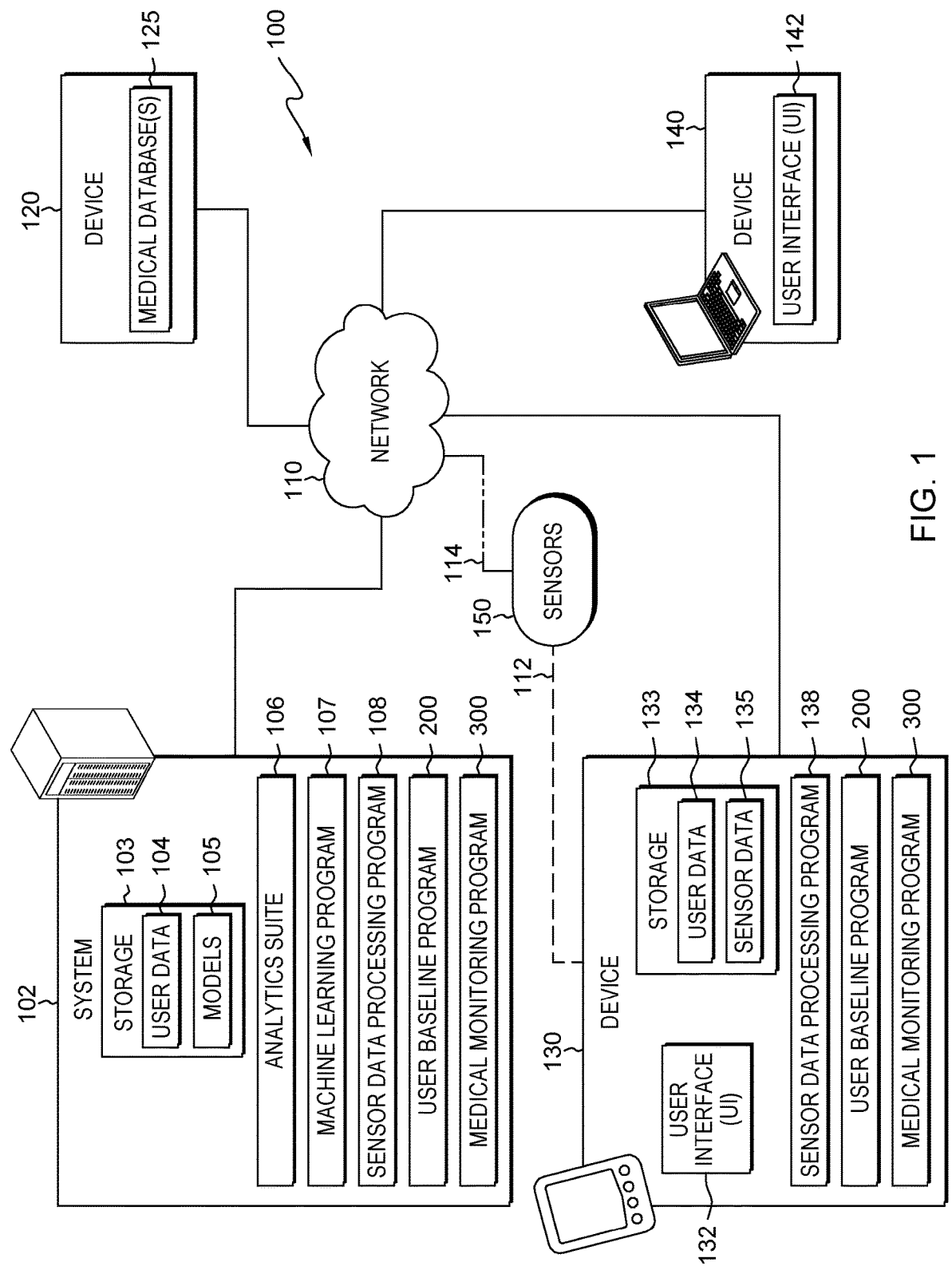
FIG. 1 illustrates a networked computing environment, in accordance with an embodiment of the present invention.

Embodiments of the present invention recognize that a set of sounds produced during eating and swallowing can be processed and analyzed to aid in diagnosing a state of health for some aspect of an individual. Some medical devices for monitoring the mechanics of eating and swallowing can be bulky, obvious, uncomfortable, and/or somewhat invasive for a user to utilize. As such, a user with a known medical condition or a potential medical condition may avoid utilizing monitoring devices until monitoring becomes an imperative, thus increasing a likelihood of negative effects to a user. Similarly, embodiments of the present invention recognize that there are a variety of methods, known in the art, for identifying and monitoring the consumption of food by an individual. For example, some mobile device applications (apps) can utilize various image recognition techniques to determine the type of food and/or beverage that an individual consumes and can estimate a quantity of food and/or beverage consumed.

Embodiments of the present invention also recognize that users are individuals and that the monitored effects of ingesting and consuming the same type, quantity, and variety of food or beverage will differ among individuals as well as differing with time for an individual based on various personal, health, and environmental factors, such as a user suffering from allergies may produce different monitoring data for the same food based on a severity of an episode of an allergy. In one example, the allergies of a user may produce sinus drainage that affects swallowing. In another example, the allergies of a user may produce breathing restrictions that reduce the taste of food and change the chewing and swallowing behaviors of the user, thereby modifying the sounds produced by chewing and swallowing. Individuals can be reluctant to seek medical diagnosis for seemingly minor changes that affect responses to daily activities, such as eating and/or a change to an appearance of an individual. As such, medical issues that develop gradually may be ignored in response to an individual discounting a change as "getting older" or misconstruing cause and effect associated with a physiological or health based change. In one example, an individual may modify a behavior to accommodate a change, such as chewing smaller portions (e.g., size) of food or cutting food into smaller pieces to ease the actions of swallowing, or sipping a beverage as opposed to previously gulping the beverage. In another example, a user may attribute a perceived change to eating or swallowing on the type or nature of a food or beverage, such as the coffee is too hot, the lack of ripeness of a fruit, or the preparation of the food. Delaying the identification of a medical issue can negatively affect economic and medical outcomes of an individual.

Therefore, embodiments of the present invention generate a plurality of models to describe various physiological responses and mechanisms related to consuming food and beverages under various conditions (e.g., normal behaviors, during an unrelated illness, etc.) by various individuals. Various models utilize sounds and other information received from a plurality of sensors as input. Some models are associated with various types of information that are obtained relating to the jaw, neck, and throat areas of a user that is monitored, such as skin (i.e., epidermis) color, texture, swelling, lumps, etc. Other models represent characteristics and responses related to the texture, consistency, temperature, etc. of food and beverages consumed as opposed to models associated with a user. Some embodiments of the present invention include interaction among models and/or combine multiple models (e.g., analytical workloads) to produce a more complex model, such as a graph workload that are utilized to determine a current state of health of the user and/or predict a change to a future state of health of the user.

Embodiments of the present invention can utilize various models of a plurality of users and a plurality of models related to consumed food and beverages, sans user information (e.g., personal information, regulated information) that are associated with various normal and abnormal medical conditions to compare and contrast the monitoring (e.g., sensor) information of a user to determine whether the monitoring information of the user indicates an unfavorable change to the state of health of the user. Embodiments of the present invention utilize the models and monitoring information to assess a degree of urgency associated with determining an unfavorable change related to the state of health of the user.

Embodiments of the present invention utilize multiple sensors and feedback mechanisms to obtain monitoring data and related contextual information. Embodiments of the present invention utilize analytics, machine learning, and cognitive methods to analyze monitoring data, predict changes to a state of health of the user, and obtain feedback from the user. Feedback from the user is utilized to generate, refine, and update one or more models that represent or predict various states of health associated with the user and/or models that represent the consumption of various foods and beverages. Embodiments of the present invention utilize a plurality of medical databases, reports, medical studies, and diagnostic information to generate models that can identify and flag potential medical issues.

Some sensors utilized by embodiments of the present invention directly monitor internal and external aspects of a user while the user consumes food and/or beverage, such as temperature, pressure, sounds, and/or movement of muscle and bone. Other sensors utilized by embodiments of the present invention indirectly monitor internal and external aspects of a user while the user consumes food and/or beverage. For example, a camera of a smartphone can capture images of the food and clothing of the user, and other sensors can monitor the environment in proximity to the user, such as air temperature. Clocks and calendars can also supply pertinent information that is utilized by embodiments of the present invention, such as adjusting an expected result of a model based on time and date. For example, during a workweek, a user may rush through eating breakfast and lunch in contrast with a weekend or a period of vacation during which the user eats at a more leisurely pace generating different results associated with similar consumption of food and beverages.

Embodiments of the present invention can utilize a plurality of sensors (e.g., monitoring components) that can be included on, about, and/or within a user. Various embodiments of the present invention utilize a distribution of sensors to improve the comfort, quality of life, and appearance (e.g., discreetly worn, camouflaged, etc.) of a user. As such, a user is more likely to utilize embodiments of the present invention due to a reduced obtrusiveness of sensors monitoring the user. Embodiments of the present invention can utilize sensors included in jewelry, such as a necklace; in apparel, such as a necktie; attachable to an item of apparel, such as within the collar of a shirt; or within the earpieces of a pair of glasses. Other embodiments of the present invention utilize one or more sensors embedded within a dental device, such as dentures or replacement teeth attached to dental implants. In addition, sensors embedded within a dental device can acquire more direct monitoring information about the temperature and consistency of items consumed by a user or a non-food item present in the mouth or throat of a user, such as a foreign object.

Embodiments of the present invention are not limited to the consumption of food or beverages. Some embodiments of the present invention can be utilized to monitor the jaw, neck, throat, and deglutition of a user under other conditions, which may indicate that the user is in distress and requires medical assistance. In an example, embodiments of the present invention may be utilized to identify an anaphylaxis reaction, a seizure, a fit of choking, an injury, an exposure to something toxic, a change to a severity of a disease within the throat, and/or a response to an equipment failure (e.g., personal protective equipment, a supply of fresh air, etc.).

Further, embodiments of the present invention recognize that by combining information from personal computing devices and medical Internet-of-things (IoT) sensors; cognitive, analytics, and machine learning; and a corpus of knowledge, models can be created to predict a state of health of a user and respond by notifying one or more individual by various devices that a change to the health of the user is predicted. Utilizing information and feedback provided by the user, embodiments of the current invention improve the scope and accuracy of models associated with the user. In addition, by anonymizing and aggregating information, feedback, and models of a plurality of users at a system (e.g., as a service) level, embodiments of the present invention continually refine and improve the accuracy of predictions of states of health of a user. As such, monitoring a user, predicting a state of health, and notifying appropriate individuals while reducing the intrusiveness of sensors and improving the quality-of-life of a user is seen to be improved in at least these aspects. Also, by implementing aspects of the present invention across a networked computing environment, more complex models associating with predicting the health of the user can be utilized in near real time as opposed to the models that can execute within the personal device of the user or utilize data uploaded during a visit to a doctor.

The present invention will now be described in detail with reference to the Figures. FIG. 1 is a functional block diagram illustrating networked computing environment 100, in accordance with embodiments of the present invention. In an embodiment, networked computing environment 100 includes: system 102, device 120, device 130, device 140, and sensors 150 all interconnected over network 110. In some embodiments, networked computing environment 100 includes one or more instances of device 120, device 130, device 140, and/or sensors 150. In one embodiment, networked computing environment 100 includes communication path 112 (dashed line), such as near-field communications or wireless communications that link one or more instances of sensors 150 to device 130. In another embodiment, networked computing environment 100 includes communication path 114 (long dash, double dot line), such as wireless communications that links one or more instance of sensors 150 to another system (e.g., system 102) or a device within networked computing environment 100 via network 110. Many modifications to the depicted environment may be made by those skilled in the art without departing from the scope of the invention as recited by the claims.

System 102, device 120, device 130, and device 140 may be: laptop computers, tablet computers, netbook computers, personal computers (PC), desktop computers, personal digital assistants (PDA), smartphones, wearable devices (e.g., digital eyeglasses, smart glasses, smart watches, smart televisions, etc.), or any programmable computer systems known in the art. In certain embodiments, system 102, device 120, device 130, and device 140 represent computer systems utilizing clustered computers and components (e.g., database server computers, application server computers, etc.) that act as a single pool of seamless resources when accessed through network 110, as is common in data centers and with cloud-computing applications. In some embodiments, device 130 is representative of two or more linked computing devices that share computing resources, such as digital eyeglasses and a smartphone, or a personal fitness/medical device and a tablet computer. In general, system 102, device 120, device 130, and device 140 are representative of any programmable electronic device or combination of programmable electronic devices capable of executing machine-readable program instructions and communicating with users of system 102, device 120, device 130, and device 140, via network 110. System 102, device 120, device 130, and device 140 may include components, as depicted and described in further detail with respect to FIG. 4, in accordance with embodiments of the present invention. In various embodiments, sensors 150 includes various electronic, computing, and networking capabilities, as depicted and described in further detail with respect to FIG. 4, in accordance with embodiments of the present invention.

System 102 includes: storage 103, analytics suite 106, machine learning program 107, user baseline program 200, and medical monitoring program 300. System 102 further includes user data 104 and models 105 within storage 103. In some embodiments, system 102 accesses/subscribes to one or more computing programs and/or databases utilized by one or more embodiments of the present invention, such as cognitive or expert system within another computing system (not shown) that is network accessible and/or one or more instances of medical database(s) 125. Storage 103 includes user data 104 and models 105. In an embodiment, storage 103 may also include various programs and/or databases, such as, but not limited to: an operating system, a file management program, a database management system, an e-mail program, visualization software, web-based applications, etc. (not shown) utilized by system 102. In various embodiments, system 102 is a cognitive computing environment.

User data 104 includes a plurality of profiles of users that utilize system 102 to generate analytical and predictive models utilized for determining a state of health, or predicting a change associated with the state of health of a user based on monitoring data corresponding to the user. User data 104 can also include and catalog other data related to a monitored user, such as information related to one or more medical professionals or services utilized by the user, emergency contact information (e.g., alternate phone numbers, e-mail addresses), insurance information, etc. In an embodiment, user data 104 is structured as a database that includes structured and unstructured information respectively associated with the plurality of users that utilize embodiments of the present invention. User data 104 may also include a catalog, cross-reference, associative array, table, etc. that links one or more models within models 105 to one or more users identified within user data 104.

In one embodiment, individual user profiles and data within user data 104 may include: demographic data; information associated with the physical condition of the user, such as height, weight, current medical issues; habits and activities of the user; dietary information; and/or identified risk factors, such as genetic testing data, previous exposure to environmental toxins, diagnosed medical conditions, job-related risk factors (e.g., known exposure items, potential exposure items). In some embodiments, user data 104 periodically receives data (e.g., one or more portions of user data 134) uploaded by device 130. In other embodiments, user data 104 periodically receives information, such as medical testing information (e.g., blood work, medical imaging data, etc.), and results of one or more visits to medical professionals from another computing system or device (e.g., device 140).

In various embodiments, user data 104 includes a corpus of structured and unstructured data that is stored within one or more databases. In some scenarios, user data 104 stores and/or catalogs a plurality of instances of unprocessed information (e.g., raw data) obtained by one or more instances of sensors 150 that are associated with a user of device 130. In other scenarios, user data 104 stores a plurality of instances of information obtained by one or more instances of sensors 150 that are associated with a user of device 130 that is processed by sensor data processing program 108. In one example, processed data from an instance of sensors 150 may be described via a Fourier transform of filtered audio signal related to a user swallowing. In another example, processed sensor (e.g., monitoring data) data within user data 104 may describe consistency information, such as a duration of chewing, a value of the pressure exerted, types of jaw motions, etc. associated with food consumed by a user of device 130 prior to swallowing the food. In addition, user data 104 can include information related to the food associated with the consistency information, such as a type of food, a quantity of food, a preparation method for the food, etc.

Models 105 includes a plurality of models related to individual users, consumptions of food and beverages, various medical conditions, etc. Models 105 may include, but are not limited to: deterministic models, probabilistic models, statistical models, stochastic models, decision trees, etc., or a combination thereof. Some models within models 105 may be dynamically generated and executed based on various rules utilized by machine learning program 107, such as utilizing information from various instances of sensors to perform a graph database analysis. Other models may dictate the aspects of sensor data processing program 108 or 138 that are to utilize process information from various instances of sensors 150.

In one embodiment, models 105 includes models of a plurality of users that were generated and refined over time, and based on information obtained by various instances of user baseline program 200. Some models within models 105 are initial models or training models derived from one or more individuals that participated in medical studies under controlled conditions to generated models associated with various types of food and beverages consumed based on texture, consistency, temperature, seasoning (e.g., salt-restrictive, bland, spicy, etc.), and/or preparation method (e.g., baked, fried, raw, etc.). In another embodiment, various models included in models 105 are utilized by medical monitoring program 300 to identify changes to a monitored user.

In various embodiments, models 105 includes models based on aggregated and anonymized data. In one scenario, models 105 includes consistency models for a plurality of foods. In one example, models 105 can include models related to food and drinks, such as potatoes prepared as crisp chips, with the crisp chips having a consistency model different from mashed potatoes with gravy. In another scenario, models 105 includes models that can identify and describe various medical conditions and associated levels of severity and progress (e.g., changes, evolution) of the medical conditions. Some models that determine or predict a state of health of a user may be generalized and utilize results of other models tuned to individual users.

Analytics suite 106 includes, but is not limited to: analytic functions, cognitive functions (e.g., image recognition, natural language processing, facial recognition, expression analysis, etc.), inferential reasoning programs, statistical analysis programs, a contextual analysis program, a database query generator, etc. In one embodiment, sensor data processing program 108 utilizes one or more aspects of analytics suite 106 to determine information associated with information received from instances of sensors 150, such as determining a distribution of occurrences and identifying statistical outliers that can bias a model. In some embodiments, aspects of analytics suite 106 are utilized by machine learning program 107 to generate a model. In other embodiments, aspects of analytics suite 106 are utilized by user baseline program 200 and/or medical monitoring program 300 to parse and analyze information input by a user.

Machine learning program 107 is a suite of techniques and algorithms utilized to generate and modify various models that are subsequently stored within models 105 of system 102 and/or user data 134 within device 130. Machine learning program 107 generates and/or modifies models that determine a state of health of a user, predicts a change to a future state of health of the user, and creates models that determine aspects of the food and/or beverages (e.g., consistency) consumed by the user based on information input by a user and/or received from various sensors. Some features of the models generated and/or modified by machine learning program 107 are previously discussed with respect to models 105.

Examples of types of models generated or modified by machine learning program 107 include, but are not limited to: graph databases, algorithms, decision trees, expert system, and/or cognitive systems. In some embodiments, machine learning program 107 includes: support vector machines, artificial neural networks, naïve Bayes classifiers, predictive analytics, and other machine learning techniques/algorithms known in the art. In another embodiment, various aspects of analytics suite 106 are utilized to augment various functions of machine learning program 107. In an example, system 102 may utilize analytics suite 106 to determine relationships and interactions among data received from instances of sensors 150 and/or information input by the user. Subsequently, machine learning program 107 utilizes information from medical database(s) 125 and the determined relationships and interactions to generate models that can determine a current state of health of a user and/or predict a future change to the state of health of the user.

Sensor data processing program 108 includes a suite of functions and programs to analyze information received from various instances of sensors 150 to extract pertinent data (e.g., preprocess) for input to one or more models of a user. In one example, sensor data processing program 108 may include: audio filters, signal processing algorithms, conversion routines (e.g., resistance to pressure, voltage to speed, etc.). In another example, sensor data processing program 108 can analyze infrasound and ultrasonic information to determine positions of food and/or various aspects of the physiology of the user. Some aspects of sensor data processing program 108 process visual information and interface with analytics suite 106 to further identify and contextualize other information, such as image recognition to identify skin color, texture, patterning, skin irregularities (e.g., a lump); identify food prior to consumption; apparel of a user; etc.

User baseline program 200 is a program that generates and/or updates models utilized to determine a state of health or to predict a change to the state of health of a monitored user. User baseline program 200 utilizes information obtained from one or more instances of sensors 150, on, about, or within the user. User baseline program 200 utilizes various data processing, cognitive, and/or analytics programs to process the information received from one or more instances of sensors 150 and information input by the user to generate models related to the user. In various embodiments, user baseline program 200 utilizes one or more models of users similar to the user as initial models that evolve and better represent the user as a corpus of information for the monitored increases with time. In some embodiments, an instance of user baseline program 200 is utilized by an instance of medical monitoring program 300 to modify one or more models related to the user utilizing various machine learning techniques to process the information received from one or more sensors and information input from the user (e.g., feedback).

In one embodiment, user baseline program 200 generates or updates models based on deglutition by a user and information, input by the user, associated with the deglutition. In another embodiment, user baseline program 200 utilizes information from other instances of sensors 150 visual information associated with the user, such as skin color. In some embodiments, user baseline program 200 queries a user to obtain contextual information utilized to analyze and interpret information from one or more instances of sensors 150 and/or contextual information to validate or modify the results of a model. In an example, user baseline program 200 may utilize various aspects of system 102 to access predefined questionnaires to be presented to a user, or dynamically generate various elements within a questionnaire based on a model used, sensor information, information related to the user, and/or information associated with one or more medical conditions of the user.

Instances of user baseline program 200 execute on device 130, system 102, or a combination thereof based on network accessibility and/or computational requirements of one or more models. In an example, if user baseline program 200 utilizes analytics suite 106 and/or machine learning program 107, then an instance of user baseline program 200 may execute within system 102 to reduce delays associated with network 110. In one scenario, user baseline program 200 executes locally on device 130 of the user. In another scenario, an instance of user baseline program 200 executes remotely on system 102 and receives information and feedback from one or more sources, such as the user of device 130 or a medical professional utilizing device 140.

In other embodiments, user baseline program 200 executes in response to one or more dictated commands. In an example, a medical professional utilizes UI 142 to execute an instance of user baseline program 200 to obtain additional information from a user based on a response generated by a model during the execution of an instance of medical monitoring program 300. In a further embodiment, an instance of user baseline program 200 executes in response to system 102 determining that new medical information (e.g., clinical studies, diagnoses, etc.) is available within medical database(s) 125 of device 120 that affects one or more models of various users. System 102 may also dictate the execution of an instance of user baseline program 200 to compare and contrast models of different users, as new machine learning/modeling algorithms are developed, etc.

Medical monitoring program 300 is a program for determining or predicting a change to a state of health of a user based on information associated with the neck and throat regions of the user. Medical monitoring program 300 inputs information associated with various instances of sensors 150 to one or more models associated with monitoring a state of health of the user. Some models utilized by medical monitoring program 300 are generated or modified by an instance of user baseline program 200. In some scenarios, an instance of medical monitoring program 300 executes on device 130 and utilizes one or more models included in user data 134 of device 130. In other scenarios, an instance of medical monitoring program 300 executes on system 102 and utilizes one or more models included in models 105 of system 102.

In various scenarios, based on the computing capabilities of device 130, an instance of medical monitoring program 300 executing on device 130 interacts with an instance of medical monitoring program 300 executing on system 102 to execute more complicated models and/or determine a level of urgency associated with a state of health of the monitored user. A level of urgency associated with the state of health of the user can range from: not urgent, a minor change to the health of the user is identified and the user is notified; very low-level of urgency, a change to the health of the user is identified with further monitoring indicated; low-level of urgency, consult a medical professional; moderate urgency, diagnostic testing and examination of the user is indicated and a doctor of the user is also notified; severe urgency, seek medical attention (i.e., visit an emergency room of a hospital); to a critical level of urgency where emergency response personnel are dispatched to the location of the user.

In one embodiment, medical monitoring program 300 utilizes models generated by user baseline program 200 to determine a change to a state of health of a user based on information relating to the consistency of food and beverage consumed by a user and the sounds generated during the consumption of food and beverage by the user. In another embodiment, if medical monitoring program 300 determines that a model does not describe the state of heath of the user, then medical monitoring program 300 can dictate the execution of an instance of user baseline program 200 to modify a model and/or obtain additional information from the user. In some scenarios, medical monitoring program 300 pauses while user baseline program 200 modifies a model. In some embodiments, medical monitoring program 300 can query medical database(s) 125 of device 120 to obtain information utilized by one or more models and/or included in results generated by one or more models. In various embodiments, based on the results obtained from one or more models, medical monitoring program 300 determines a level of urgency associated with the state of health of the user and communicates responses (e.g., notifications) to the user, a medical professional associated with the user, and/or a medical service.

In one embodiment, system 102 communicates through network 110 to device 120 and device 130. In some embodiments, system 102 communicates with one or more other computing systems and/or computing resources, such as a web server, an e-mail server, a network of health care service providers, etc. (not shown) via network 110. Network 110 can be, for example, a local area network (LAN), a telecommunications network, a wireless local area network (WLAN), such as an intranet, a wide area network (WAN), such as the Internet, or any combination of the previous and can include wired, wireless, or fiber optic connections. In general, network 110 can be any combination of connections and protocols that will support communications between system 102, device 120, and device 130, in accordance with embodiments of the present invention. In various embodiments, network 110 operates locally via wired, wireless, or optical connections and can be any combination of connections and protocols (e.g., personal area network (PAN), near field communication (NFC), laser, infrared, ultrasonic, etc.). In other embodiments, network 110 includes communication path 114 that enables an instance of sensors 150 to transmit data to system 102. Similarly, one or more aspects of network 110 may be utilized to generate communication path 112 to enable one or more instance of sensors 150 to transmit information to device 130.

Device 130 may include user interface (UI) 132, storage 133, sensor data processing program 138, user baseline program 200, and medical monitoring program 300. In some scenarios, device 130 is a computing device tailored for various medical monitoring functions associated with a user. In other scenarios, device 130 is a more common computing device (e.g., a smartphone, a tablet computer, etc.) utilized by a user that is adapted to include various medical monitoring functions for the user. Storage 133 may be comprised of a combination of volatile and non-volatile storage media. Storage 133 includes user data 134 and sensor data 135. In addition, storage 133 also stores various programs and data (not shown) utilized by device 130. Examples of programs that storage 133 may include are: an operating system, a web browser, an office productivity suite, a communication program, a natural language processing (NLP) program, one or more applications (apps), such as an instant messaging (IM) app, a telephone app, and a video chat app, etc. Examples of data that storage 133 may include, but are not limited to are: user preferences, a web browsing history, video files, information utilized to identify and locate device 130, etc. In some embodiments, device 130 utilizes network 110 to communicate with another computing system (not shown) to obtain environmental factors in proximity to the user, such as temperature, barometric pressure, pollen count, etc.

In one embodiment, UI 132 may be a graphical user interface (GUI) or a web user interface (WUI), and UI 132 can display text, documents, forms, web browser windows, user options, application interfaces, and instructions for operation, and include the information, such as graphic, text, and sound that a program presents to a user. In addition, UI 132 controls sequences/actions that the user employs to input and/or modify user data, input data, and provide feedback to user baseline program 200, and/or respond to one or more notifications generated by medical monitoring program 300. In various embodiments, UI 132 displays one or more icons representing applications that a user can execute via network 110, and various programs of system 102 and/or other computing systems (not shown) accessible via network 110.

In some embodiments, a user of device 130 can interact with UI 132 via a singular device, such as a touch screen (e.g., display) that performs both input to a GUI/WUI, and as an output device (e.g., a display) presenting a plurality of icons associated with apps and/or images depicting one or more executing software applications. In other embodiments, a software program (e.g., a web browser) can generate UI 132 operating within the GUI environment of device 130. UI 132 accepts input from a plurality of input/output (I/O) devices (not shown) including, but not limited to, a tactile sensor interface (e.g., a touch screen, a touchpad), a natural user interface (e.g., voice control unit or a motion capture device), and virtual or augmented reality interfaces utilizing on eye tracking, a cyberglove, a head-up display, etc. In addition to the audio and visual interactions, UI 132 may receive input in response to a user of device 130 utilizing natural language, such as written words or spoken words, device 130 identifies as information and/or commands.

User data 134 includes one or more individual profiles of users that utilize device 130 to monitor the respective states of health of the monitored users. User data 134 can also include other data related to a monitored user, such as information related to one or more medical professionals or services utilized by the user, emergency contact information (e.g., alternate phone numbers, e-mail addresses), insurance information, etc. In one embodiment, a user data 134 includes a plurality of models associated with the determining/predicting a state of health of the user, models associated with the consumption of food and beverage, and other information that is substantially similar to the data corresponding to the monitored user stored within a respective profile of the user included in user data 104 of system 102. User data may also include demographic data; information associated the physical condition of the user, such as height, weight, current medical issues; habits and activities of the user; dietary information; identified risk factors, such as genetic testing data, etc. In some embodiments, user data 134 does not include all the models associated with a user or models related to the consumption of food or beverages. Models may be downloaded from system 102 as needed. In various embodiments, user data 134 periodically receives information from device 140, such as an updated medical history or results of visits to a medical professional.

Sensor data 135 includes raw and/or processed information from various instances of sensors 150. In one embodiment, sensor data 135 includes data received from an instance of sensors 150 via communication path 112. In some embodiments, sensor data 135 is periodically uploaded to system 102 for inclusion within a respective user profile in user data 104. Upon storage within system 102, various portions of sensor data 135 are deleted to prevent device 130 from becoming storage constrained. In one embodiment, sensor data 135 buffers information from various instances of sensors 150 prior to processing by sensor data processing program 138.

Sensor data processing program 138 may include capabilities similar to sensor data processing program 108 of system 102. In some embodiments, based on the computational capabilities of device 130, sensor data processing program 138 offloads the processing of sensor data to sensor data processing program 108 executing on system 102.

Sensors 150 are representative of one or more sensors that monitor various aspects of a user. Instances of sensors 150 may be battery powered, inductively powered, or self-powered (e.g., by motion, by a piezoelectric effect, etc.). Some instances of sensors 150 can acquire a variety of sound-based monitoring information associated with a user of device 130. In one example, sound-based monitoring information may include audible sounds, sub-audible sounds, infra-sound, and ultrasound when paired with an ultrasonic transducer. Other instance of sensors 150 can include sensors that acquire other information, such as temperature, pressure, visual (e.g., pictures, video, visible colors, non-visible colors, etc.), movement, orientation, pulse, perspiration, neural activity (e.g., electrical activity) associated with one or more muscles, and/or tension related to one or more muscles. Visual information acquired by an instance of sensors 150 may include images of food and beverages consumed by a user, images of the skin color and skin condition of the user, images of apparel worn by the user, and gestures and expressions of the user. In one embodiment, user baseline program 200 of device 130 receives information associated with one or more instances of sensors 150 is included in device 130.

In some embodiments, instances of sensors 150 are associated with acquiring information associated with the consumption of food or beverage. In other embodiments, other instances of sensors 150 acquire information associated with factors within proximity to the user, such as temperature, barometric pressure, humidity, etc. In various embodiments, information obtained from one or more instances of sensors 150 is processed by one or more aspects of a sensors data processing program, such as sensor data processing program 138 of device 130, to extract data that is input to one or more models.

In one embodiment, one or more instances of sensors 150 (e.g., a camera, a microphone) are embedded within device 130, such as a mobile phone or a personal fitness device. In another embodiment, one or more instances of sensors 150 are included in another electronic or computing device (not shown) that communicates with or is linked to device 130, such as a pair of smart glasses that utilize various capabilities of a smartphone or tablet computer (e.g., device 130). In some embodiments, one or more instances of sensors 150 communicates information to device 130 via communication path 112. Some instances of sensors 150 directly monitor and obtain information associated with a user, an environment in proximity to the user, one or more activities of the user, and/or items associated with a user, such as consumables (e.g., food, beverages, etc.). In other instances, sensors 150 may be embedded (e.g., hidden) within apparel, jewelry, accessories, etc. Still other instances, sensors 150 may be applied to the anatomy of a user and camouflaged with a covering matching the texture and tone of the skin of the user. In a further embodiment, some instances of sensors 150 are not employed by the user unless directed to do so by one or more aspects of the current invention and/or as directed by one or more medical professionals.

Device 140 includes user interface (UI) 142 and may also include various programs and data (not shown) utilized by device 140. Examples of programs associated with device 140 may include: an operating system, a web browser; an office productivity suite; a database query program; a natural language processing program; one or more applications (apps), such as an instant messaging (IM) app, a telephone app, and a video chat app; software to review and edit models; etc. Examples of data associated with device 140 may include, but are not limited to patient (i.e., user) records, emergency contacts, medical images, etc.

In an embodiment, device 140 is representative of a device associated with a medical professional. In some scenarios, device 140 is associated with a provider of medical services, such as an office of a doctor for the user of device 130. In another scenario, device 140 is associated with an emergency response provider, such as a medical alert service or an ambulance service. In another embodiment, device 140 is a client device by a group or a service provider that utilizes system 102 to generate models that analyze information received from various instances of sensors 150 during the monitoring of a plurality of users, and models for predicting a state of health of a user based on the received sensor information. In addition, device 140 can enable the group or the administrator of system 102 to access medical database(s) 125 of device 120 to review and curate the corpus of medical information therein for access by system 102 and utilization within one or more models of users.

In one embodiment, UI 142 includes various functionalities and capabilities described previously with respect to UI 132 of device 130. In another embodiment, UI 142 includes additional capabilities utilized to access aspects of system 102, device 120, and/or one or more medical services. In an example, a doctor utilizes UI 142 to review a notification generated by an instance of medical monitoring program 300 to determine whether to contact a user of device 130 to verify a state of health of a user, to notify another individual associated with the user (e.g., an emergency contact), and/or notify a medical service to check on the user.

Figure 2:
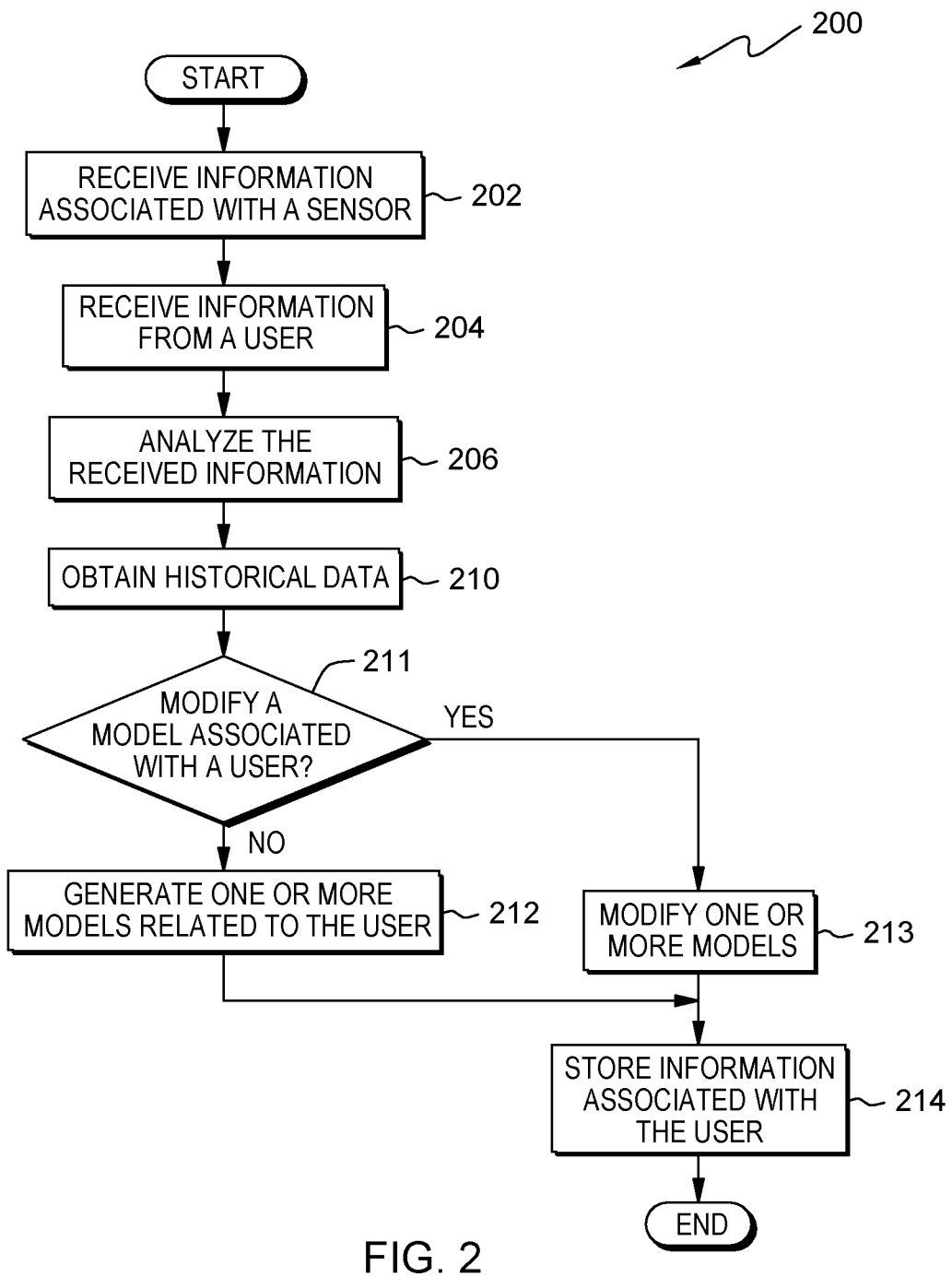
FIG. 2 depicts a flowchart of the operational steps of a user baseline program, in accordance with an embodiment of the present invention.

FIG. 2 is a flowchart depicting operational steps for user baseline program 200, a program that generates and/or modifies models utilized to predict or determine a state of health for a monitored user, in accordance with embodiments of the present invention. In various embodiments, user baseline program 200 obtains information from instances of sensors 150 and information input by the user associated with one or more actions, observations, and/or feedback associated with the user and the sensors monitoring the user to aggregate within a corpus of information used for generating models associated with the user. In an embodiment, user baseline program 200 executes at various times or as dictated by the user.

In some embodiments, instances of user baseline program 200 execute concurrently with one or more instances of medical monitoring program 300. In other embodiments, user baseline program 200 executes in response to certain conditions, such as medical monitoring program 300 initiating the execution of an instance of user baseline program 200 to obtain user feedback and modify a model. In a further embodiment, an instance of user baseline program 200 executes on system 102 on a periodic basis or as dictated by administrators of system 102 and/or medical professionals that utilize aspects of the present invention to monitor patients.

In step 202, user baseline program 200 receives information associated with a sensor. User baseline program 200 receives information from a plurality of instances of sensors 150 associated with a monitored user. Sensor-based user information received by user baseline program 200 may include images of the food and beverages consumed by a user, images of the appearance (e.g., skin color and condition, apparel worn by the user, gestures and expressions of the user). In one embodiment, user baseline program 200 of device 130 receives information associated with one or more instances of sensors 150 is included in device 130. In another embodiment, user baseline program 200 of device 130 receives information associated with one or more instances of sensors 150 via communication path 112. In another embodiment, user baseline program 200 of system 102 receives information associated with one or more instances of sensors 150 via communication path 114 and network 110.

Figure 3:
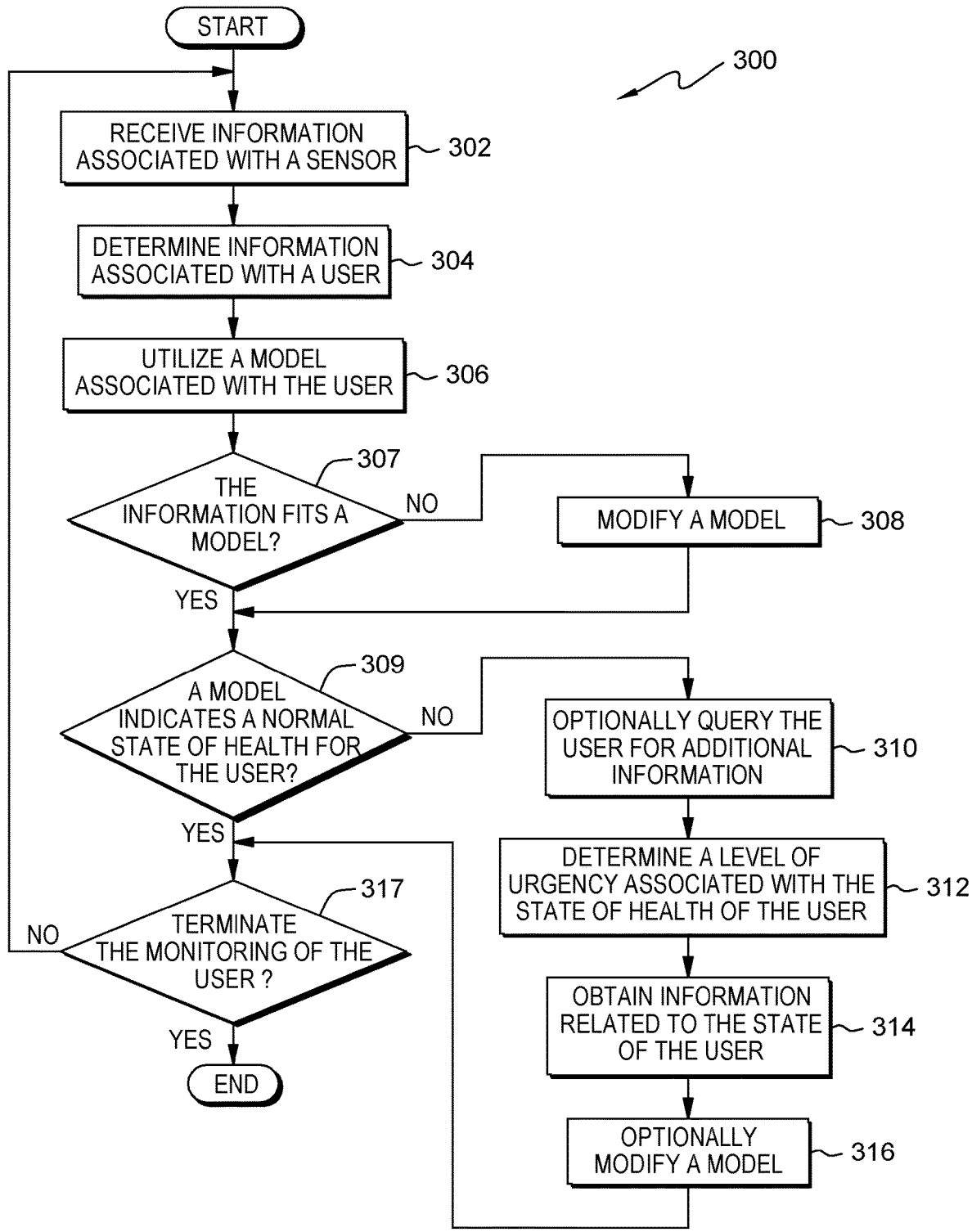
FIG. 3 depicts a flowchart of the operational steps of a medical monitoring program, in accordance with an embodiment of the present invention.

In some embodiments, user baseline program 200 obtains information associated with one or more sensors received during the execution of an instance of medical monitoring program 300 (referring to FIG. 3, step 302). In some scenarios, user baseline program 200 obtains information associated with one or more sensors included in sensor data 135 of device 130. In other scenarios, user baseline program 200 obtains information associated with one or more sensors stored in user data 104 of system 102. In various scenarios, user baseline program 200 obtains information associated with one or more sensors from a combination of storage locations.

In step 204, user baseline program 200 receives information from a user. In one embodiment, during a training period, a user utilizes device 130 to input information related to a consumption of food and/or beverage. User baseline program 200 may utilize UI 132 to present a questionnaire to the monitored user of device 130 to obtain information. The questionnaire includes queries associated with the current state of health of a user, a location (e.g., sitting outdoors, in a restaurant, riding in a vehicle, etc.), a current or historic level of stress, food or beverage to consume, the attire of the user, etc.

In another embodiment, user baseline program 200 receives information from a user based on processing one or more queries associated with various aspects of medical monitoring program 300. In one scenario, user baseline program 200 receives information from a user related to medical monitoring program 300 determining that the information (e.g., sensor information and/or user input information) does not fit a model (referring to FIG. 3, No branch of decision step 307). In an example, medical monitoring program 300 expects a range of sensor information (i.e., values) for a model based on one set of information, such as a food choice, input by the user. However, the actual food consumed by the user is not associated with the input information. In another scenario, user baseline program 200 receives information from a user in response to medical monitoring program 300 determining that a model associated with a user does not indicates a normal state for the user (referring to FIG. 3, No branch of decision step 309), such as the user flagging a false alarm.

Still referring to step 204 in some embodiments, user baseline program 200 receives information from another individual based on medical monitoring program 300 determining or predicting one state and/or level of urgency associated with a user (referring to FIG. 3, No branch of decision step 309). However, the actual state of the user differs from the state of the user determined and/or predicted by one or more models. In one example, a doctor reviews a notification generated by medical monitoring program 300 and the received sensor data, and the doctor determines that a model is generating a false-positive result. If the doctor contacts the user and verifies that the model generated a false-positive result, then the doctor may flag the model for modifying. Alternatively, based on feedback from the user, medical monitoring program 300 may determine that a model underestimates a level of urgency associated with a predicted change in the state of health of the user.

In step 206, user baseline program 200 analyzes the received information. In one embodiment, user baseline program 200 utilizes an instance of sensor data processing program 138 of device 130 or sensor data processing program 108 of system 102 to analyze and/or preprocess the information associated with one or more instances of sensors 150. In another embodiment, user baseline program 200 utilizes one or more aspects of analytics suite 106 to process the received information, such as an NLP program to parse and analyze information input by the user, such as a response to a questionnaire presented by UI 132. The responses to the questionnaire are subsequently utilized during the generation or modification of one or more models. In various embodiments, user baseline program 200 utilizes one or more aspects of analytics suite 106 to perform image recognition to determine information related to one or more received images, such as identifying a quantity and type of food consumed by the user, or skin-related information (e.g., flushing, pigmentation change, etc.). In other embodiments, user baseline program 200 analyzes information from other sources, such as weather conditions, pollen counts, a time & date function, etc.

In step 210, user baseline program 200 obtains historical data. Historical data refers to monitoring data and medical-related information associated with a user. Historical data may consist of the following types of information: sounds, models, sensor information, associated times & dates, locations of the user, user information, items of food or beverages consumed, information obtained from medical database(s) 125 of device 120, medical history of the user, diagnostic testing data related to the user, etc. In one embodiment, if device 130 is storage constrained, then user baseline program 200 obtains one or more models from models 105 of system 102 based on a corpus of information associated with the user, user input, and/or preliminary sensor information that indicates a consumption of food or beverage. In another embodiment, user baseline program 200 utilizes a clock or calendar function to determine a set of models to be available on device 130. In some embodiments, in response to medical monitoring program 300 determining that a model is modified, user baseline program 200 obtains historical information from user data 104 of system 102, such as sounds, models, sensor information, etc. for utilization by machine learning program 107 to modify one or more models (step 213).

In decision step 211, user baseline program 200 determines whether to modify a model associated with a user. In one embodiment, user baseline program 200 determines to make a modification to a model associated with a user based on one or more actions of an instance of medical monitoring program 300 (e.g., determining that a model does not describe a state of the user). In another embodiment, user baseline program 200 determines to make a modification to a model associated with a user based on receiving updated information from one or more sources, such as new/updated information within medical database(s) 125 of device 120, or models of similar users are updated within system 102. In some embodiments, user baseline program 200 receives a dictate (e.g., a command, a response) from a medical professional via UI 142 of device 140 to modify (e.g., update) a model. In other embodiments, user baseline program 200 generates one or more models related to the user as opposed to modifying a model. For example, user baseline program 200 generates a model during a training period associated with the user or in response to determining that a user consumes a food or beverage that is not modeled. In an alternative embodiment, if user baseline program 200 does not have sufficient data and information to modify a model or generate a model, then user baseline program 200 terminates.

Responsive to determining not to modify a model associated with a user a model associated with the user (No branch, decision step 211), user baseline program 200 generates one or more models related to the user (step 212).

In step 212, user baseline program 200 generates one or more models related to the user. User baseline program 200 may utilize a combination of functions and/or programs associated with machine learning program 107 and analytics suite 106 to generate one or more models related to the user. In one embodiment, user baseline program 200 generates models representing the consistency of food and/or beverage consumed by the user under known conditions and a user input state of health. In another embodiment, user baseline program 200 generates a model representative of a state of health of the user by utilizing one or more food models, information within medical database(s) 125 of device 140, and information input by the user. In some embodiments, user baseline program 200 generates a model related to a user by tailoring a model, stored within models 105, associated with one or more similar users. In a further embodiment, user baseline program 200 transmits a query and one or more models to a medical professional via device 140 for review, modifying, and approval.

Referring to decision step 211, responsive to determining to modify one or more models (Yes branch, decision step 211), user baseline program 200 modifies one or more models (step 213).

In step 213, user baseline program 200 modifies one or more models. User baseline program 200 may utilize a combination of functions and/or programs associated with machine learning program 107 and analytics suite 106 to modify, update, or replace one or more models. In various embodiments, user baseline program 200 utilizes information obtained by medical monitoring program 300 to modify a model. In one embodiment, user baseline program 200 modifies one or more models representing the consistency of food and/or beverage consumed by the user under conditions and states of health not previously observed or cataloged. In another embodiment, user baseline program 200 modifies a model that is not necessarily representative of the state of health of the user. In some embodiments, user baseline program 200 modifies a model based on new or updated information within medical database(s) 125 of device 120. In a further embodiment, user baseline program 200 transmits a query and one or more models to a medical professional via device 140 for review, modifying, and approval.

In step 214, user baseline program 200 stores information associated with the user. In one embodiment, user baseline program 200 stores the data received from one or more sensors and the information received from a user within one or more storage locations, such as user data 104 of system 102, user data 134, and/or sensor data 135 of device 130. In another embodiment, user baseline program 200 stores one or more generated models related to the user within one or more storage locations, such as user data 104 of system 102, user data 134, and/or sensor data 135 of device 130. In some embodiments, user baseline program 200 periodically uploads information from portions of sensor data 135 of device 130 prior to deleting sensor information to reclaim storage space on system 130. In other embodiments, another individual, such as a medical professional, can override which information is stored by user baseline program 200.

FIG. 3 is a flowchart depicting operational steps for medical monitoring program 300, a program for determining a state of health associated with the jaw, neck, and throat regions of a monitored user, in accordance with embodiments of the present invention. In various embodiments, medical monitoring program 300 determines the current state of health of a user or predicts a change to the state of health of the user based on sensors recording various sounds during deglutition by the user. In some embodiments, medical monitoring program 300 utilizes other types of sensor information, such as sound as input(s) to one or more models to determine the current state of health of a user or predict a change to the state of health of the user. An instance of medical monitoring program 300 can execute concurrently with one or more instances of user baseline program 200.

In step 302, medical monitoring program 300 receives information associated with a sensor. Medical monitoring program 300 receives information from one or more instances of sensors 150 associated with a user of device 130 as previously discussed with respect to FIG. 2, step 202. In some embodiments, medical monitoring program 300 receives atypical sensor information that was not identified during the training and generation of one or more models, such as an indication of choking; or the user utilizing a back slap, chest thump, or an intake of extra liquid (i.e., a beverage) to facilitate swallowing.

In step 304, medical monitoring program 300 determines information associated with a user. In an embodiment, medical monitoring program 300 determines information associated with a user of device 130 as previously discussed with respect to FIG. 2, step 204. In some embodiments, medical monitoring program 300 determines information (e.g., analyzes data) associated with a user of device 130 as previously discussed with respect to FIG. 2, step 206. In various embodiments, based on the determined information, medical monitoring program 300 identifies the one or more models to utilize with respect to the current conditions associated with the user. In an example, based on an image recognition program (not shown) determining the food for consumption by the user and information input by the user, medical monitoring program 300 identifies one or more models to utilize for determining the state of health of the user or predicting a change to the state of health of the user. The identified models may be included within user data 134 of device 130 and/or models 105 of system 102.

In step 306, medical monitoring program 300 utilizes a model associated with a user. In one embodiment, medical monitoring program 300 utilizes one or more identified models to obtain results that describe (e.g., predict) the anticipated information from various instances of sensors 150 based on the food and/or beverage to be consumed by the user and other factors associated with the user, such as time & date, location, environmental factors, and apparel of the user. In another embodiment, an instance of medical monitoring program 300 executing on device 130 can download models as needed from system 102 that are not stored within user data 134. In some embodiments, medical monitoring program 300 inputs the results derived from models associated with consumption of food and beverages to one or more models associated with determining a state of health of the user and/or predicting a change to the state of health of the user. In other embodiments, medical monitoring program 300 utilizes one or more identified models associated with the user to determine whether the information received from one or more instances of sensors 150 matches the expected range of sensor information (i.e., values).

In decision step 307, medical monitoring program 300 determines whether the information fits a model. In one embodiment, medical monitoring program 300 determines, based on the information received and analyzed from one or more instances of sensors 150, that the information does not fit a model. In one example, medical monitoring program 300 utilizes a model based on the input of the user. However, one or more attributes associated with food and/or beverage (e.g., an expected range of sensor information/values), such as consistency, bite force, chewing duration, etc., does not match output of actions that the user performs to consume the food and/or beverages input by the user. In another example, medical monitoring program 300 determines that information associated with the user is not included in the model, such as the user eating while wearing constricting neckwear, or the user eating in an orientation that was not modeled (e.g., laying horizontal). In another embodiment, medical monitoring program 300 determines that a model does not exist for the information input, such as a new type of food. In some embodiments, medical monitoring program 300 includes one or more override conditions that bypass (i.e., skip) decision step 307 and trigger the No branch of decision step 309, such as an episode of choking that exceeds a threshold value, such as 5 seconds; or a change to the color of the skin of a user that may indicate the occurrence of cyanosis.

In response to determining that the information does not fit a model (No branch, decision step 307), medical monitoring program 300 modifies one or more models (step 308).

In step 308, medical monitoring program 300 modifies a model. In one embodiment, medical monitoring program 300 executes an instance of user baseline program 200 to modify one or more models and/or generate one or more new models associated with the food and/or beverage consumed by the user. In another embodiment, medical monitoring program 300 executes an instance of user baseline program 200 to modify one or more models associated with the state of the monitored user and additional information input by the user.

Referring to decision step 307, in response to determining that the information fits a model (Yes branch, decision step 307), medical monitoring program 300 determines whether a model indicates a normal state of health for the user (decision step 309).

In decision step 309, medical monitoring program 300 determines whether a model indicates a normal state for the user. Medical monitoring program 300 can review and analyze the results of multiple models in parallel. Different models are utilized to determine or predict various changes to a state of health of the user. In various embodiments, medical monitoring program 300 determines that a single abnormal result (e.g., a state of health or a predicted change to the state of health of the user) is obtained and triggers the No branch of decision step 309. In one embodiment, medical monitoring program 300 determines that a model describes a normal state of health for a user. In another embodiment, medical monitoring program 300 determines whether a model, modified or newly generated by user baseline program 200 (step 308), describes a normal state of health for the user.

In response to determining that a model does not indicate a normal state for the user (No branch, decision step 309), medical monitoring program 300 optionally queries the user for additional information (step 310). In some embodiments, based on which one or more models do not indicate a normal state of health for the user, medical monitoring program 300 modifies the execution order of steps 310 through 316.

In step 310, medical monitoring program 300 optionally queries the user for additional information. In one embodiment, medical monitoring program 300 queries the monitored user via device 130 to determine whether information associated with one or more sensors is correct. In one example, the user may be wearing a pair of glasses with one or more embedded sensors on top of the head of the user as opposed to the face of the user. Medical monitoring program 300 may determine that the results associated with the sensors of the glasses are suspect and contact the user via device 130 to determine whether the glasses of the monitored user are worn correctly prior to making further determinations. In another example, medical monitoring program 300 queries the user to determine a reason for biased sensor information, such as chewing preferentially on one side of the mouth of the user. In some embodiments, medical monitoring program 300 queries a user less frequently based on one or more modified models. In an example, machine learning program 107 identifies user actions and/or behaviors that potentially trigger a query and includes the identified user actions and/or behaviors to one or more models of models 105 and/or models within user data 134.

In another embodiment, medical monitoring program 300 queries a user to obtain information that may indicate a reason that a model predicts a change to the state of health of the user. In an example, medical monitoring program 300 queries a user to determine whether the user is afflicted with a minor medical condition, such as an episode of allergies, an occurrence of a cold or flu, stomach problems, etc.

In step 312, medical monitoring program 300 determines a level of urgency associated with the state of health of the user. In addition to determining a level of urgency, medical monitoring program 300 can transmit one or more notifications related to the current or predicted future state of health of the user. Based on the level of urgency, medical monitoring program 300 can send a notification to the user, one or more medical professionals, and/or an emergency medical service. In one embodiment, medical monitoring program 300 determines a level of urgency associated with the state of health of the user based on a known medical condition of the user and one or more results generated by models associated with the user. In one example, medical monitoring program 300 may notify a user, via device 130, to contact the primary care provider (PCP) for the user and provide the user with an indication of the level of urgency while excluding one or more possible diagnoses. However, medical monitoring program 300 also notifies the PCP via UI 142 of device 140 with a determined level of urgency and various possible diagnoses related to the state of health of the user. Medical monitoring program 300 thereby enables the PCP to order diagnostic tests for the user prior to the user visiting the office of the PCP.

In another embodiment, medical monitoring program 300 queries medical database(s) 125 of device 120 to determine a level of urgency associated with the determined state of health of the user. In an example, medical monitoring program 300 utilizes the results of one or more models and associated sensor information to query medical database(s) 125 of device 120 to determine a level of urgency associated with the current state of heath of the user. In some embodiments, medical monitoring program 300 queries medical database(s) 125 of device 120 to determine a level of urgency associated with a predicted change to the state of health of the user. In an example, medical monitoring program 300 predicts the possibility of a change to the state of the health of the user. However, medical monitoring program 300 does not have sufficient information to propose one or more possible diagnosis with a high level of confidence. Therefore, medical monitoring program 300 transmits a notification to a medical professional associated with the user to obtain further information related to the state of the user (step 314), such as ordering diagnostic testing.

In step 314, medical monitoring program 300 obtains information related to the state of the user. In some embodiments, medical monitoring program 300 queries a user via UI 132 to obtain information related to the state of the user. Medical monitoring program 300 communicates a notification of a determined or predicted state of health (e.g., an assessment) associated with the user and a corresponding level of urgency related to the health of the user. Medical monitoring program 300 may obtain information similar to the information discussed with respect to step 310. In addition, medical monitoring program 300 may query the user for more specific information related to aspects of the level of urgency as perceived by the user, such as an opinion related to the accuracy of the level of urgency or other information may indicate inaccuracies within one or more models. In other embodiments, if medical monitoring program 300 cannot obtain information related to the user from the user, then medical monitoring program 300 communicates with another individual, such as an emergency contact, or a known individual in proximity to the user (e.g., based on location information and a social networking application). In various embodiments, medical monitoring program 300 obtains additional information related to the state of the user from one or more medical services, such as a doctor of a user, a medical testing location, emergency personnel interacting with the user, etc.

In step 316, medical monitoring program 300 optionally modifies a model. In one embodiment, if medical monitoring program 300 determines that a model produced a false-positive result, such a predicting a negative change to the health of the user or over estimating the level of urgency; then, medical monitoring program 300 executes an instance of user baseline program 200 to modify a model. In another embodiment, if medical monitoring program 300 determines that a model underestimated the level of urgency for a state of health of the user, then medical monitoring program 300 executes an instance of user baseline program 200 to modify a model. In some embodiments, medical monitoring program 300 modifies one or more models associated with the consumption of food and/or beverage. In other embodiments, medical monitoring program 300 modifies a model based on a dictate (e.g., input, command) by a medical professional. Subsequently, medical monitoring program 300 determines whether to terminate the monitoring of the user (decision step 317).

Referring to decision step 309, responsive to determining that a models indicates a normal state of health of the user (Yes branch, decision step 309), medical monitoring program 300 determines whether to terminate the monitoring of the user (decision step 317).

In decision step 317, medical monitoring program 300 determines whether to terminate the monitoring of the user. In some embodiments, medical monitoring program 300 continually monitors a user. In other embodiments, to conserve battery life of device 130, medical monitoring program 300 terminates monitoring the user based on one or more triggers, such as a time of day, lack of activity by the user, between sampling periods while the user is not consuming food or beverage, etc. In one example, medical monitoring program 300 terminates monitoring the user based on a period after the user stops consuming food or beverage, a clock function deactivating at a preprogrammed time slots, or as dictated by the user (e.g., via UI 132). In another example, medical monitoring program 300 terminates monitoring the user based on the user removing one or more instances of sensors 150 from the person of the user. In one embodiment, medical monitoring program 300 does not terminate monitoring the user in response to determining that device 130 is connected to a persistent power source, such as a charger.

Responsive to determining not to terminate monitoring the user (No branch, decision step 317), medical monitoring program 300 loops to step 302.

Responsive to determining to terminate monitoring the user (Yes branch, decision step 317), medical monitoring program 300 stops executing.

Figure 4:
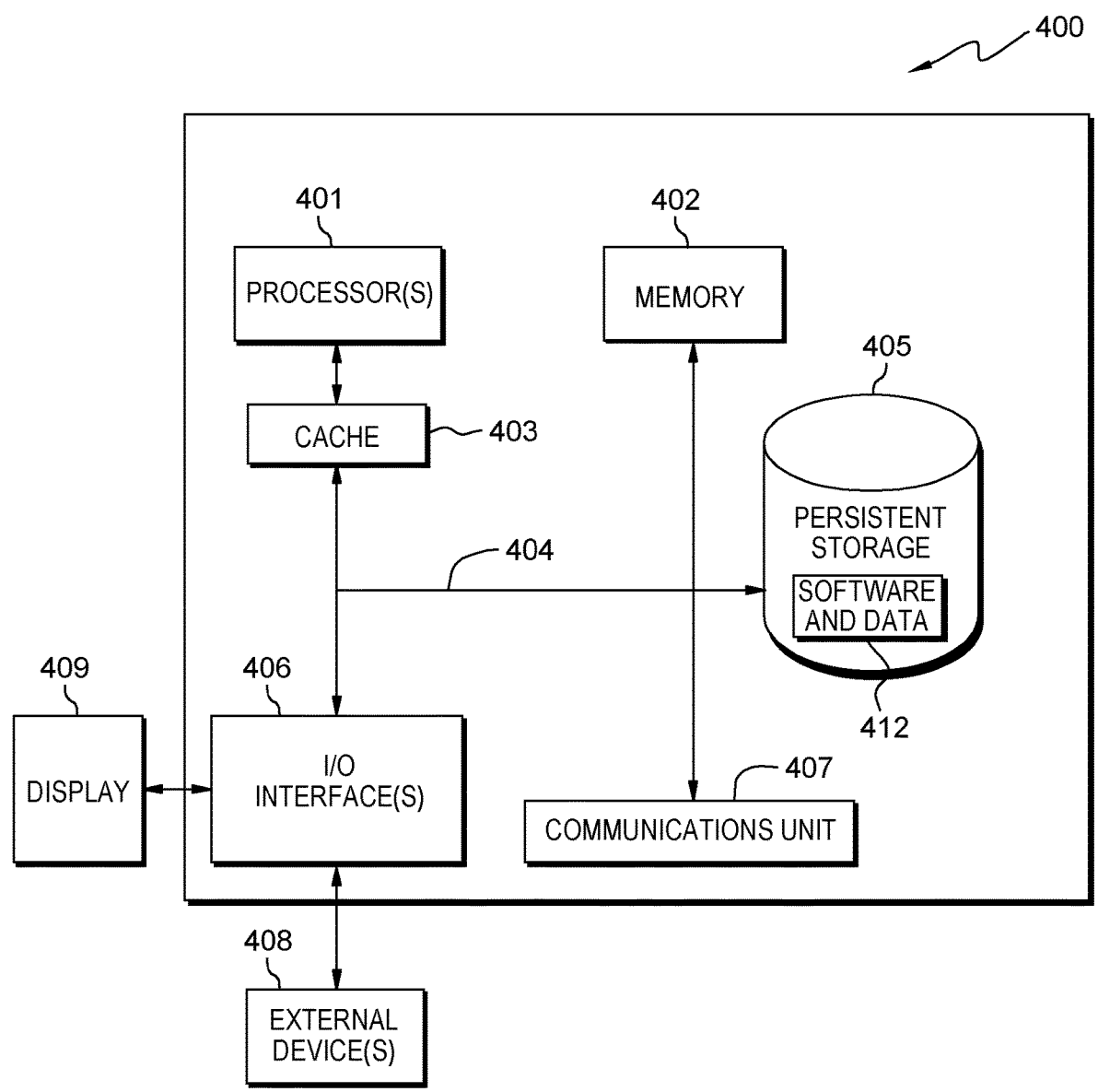
FIG. 4 is a block diagram of components of a computer, in accordance with an embodiment of the present invention.

FIG. 4 depicts a block diagram of computer system 400, which is representative of system 102, device 120, device 130, and device 140. Computer system 400 is an example of a system that includes software and data 412. Computer system 400 includes processor(s) 401, memory 402, cache 403, persistent storage 405, communications unit 407, input/output (I/O) interface(s) 406, and communications fabric 404. Communications fabric 404 provides communications between memory 402, cache 403, persistent storage 405, communications unit 407, and I/O interface(s) 406. Communications fabric 404 can be implemented with any architecture designed for passing data and/or control information between processors (such as microprocessors, communications and network processors, etc.), system memory, peripheral devices, and any other hardware components within a system. For example, communications fabric 404 can be implemented with one or more buses or a crossbar switch. In some embodiments, computer system 400 is also representative of some instances of sensors 150.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of processor(s) 401 by holding recently accessed data, and data near recently accessed data, from memory 402.

Program instructions and data used to practice embodiments of the present invention may be stored in persistent storage 405 and in memory 402 for execution by one or more of the respective processor(s) 401 via cache 403. In an embodiment, persistent storage 405 includes a magnetic hard disk drive. Alternatively, or in addition to a magnetic hard disk drive, persistent storage 405 can include a solid-state hard drive, a semiconductor storage device, a read-only memory (ROM), an erasable programmable read-only memory (EPROM), a flash memory, or any other computer readable storage media that is capable of storing program instructions or digital information. In an embodiment, with respect to system 102, storage 103 is included in persistent storage 405 and with respect to device 130 storage 133 is included in persistent storage 405.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405. Software and data 412 are stored in persistent storage 405 for access and/or execution by one or more of the respective processor(s) 401 via cache 403 and one or more memories of memory 402. With respect to system 102, software and data 412 includes: user data 104, models 105, analytics suite 106, machine learning program 107, sensor data processing program 108, user baseline program 200, medical monitoring program 300, and various programs (not shown). With respect to device 120, software and data 412 includes medical database(s) 125 and various programs and data (not shown). With respect to device 130, software and data 412 includes user data 134, sensor data 135, sensor data processing program 138, user baseline program 200, medical monitoring program 300, and various programs and data (not shown). With respect to device 140, software and data 412 includes UI 142 and various programs and data (not shown). With respect to some instances of sensors 150, software and data 412 may be representative of firmware (not shown) utilized to operate an instance of sensors 150.

Communications unit 407, in these examples, provides for communications with other data processing systems or devices, including resources of system 102, device 120, device 130, device 140, and instances of sensors 150. In these examples, communications unit 407 includes one or more network interface cards and/or one or more wireless communication units. Communications unit 407 may provide communications through the use of either or both physical and wireless communications links. Program instructions and data used to practice embodiments of the present invention may be downloaded to persistent storage 405 through communications unit 407.

I/O interface(s) 406 allows for input and output of data with other devices that may be connected to each computer system. For example, I/O interface(s) 406 may provide a connection to external device(s) 408, such as a keyboard, a keypad, a touch screen, one or more instance of sensors 150, and/or some other suitable input device. External device(s) 408 can also include portable computer readable storage media, such as, for example, thumb drives, portable optical or magnetic disks, and memory cards. Software and data 412 used to practice embodiments of the present invention can be stored on such portable computer readable storage media and can be loaded onto persistent storage 405 via I/O interface(s) 406. I/O interface(s) 406 also connect to display 409.

Display 409 provides a mechanism to display data to a user and may be, for example, a computer monitor. Display 409 can also function as a touch screen, such as the display of a tablet computer or a smartphone.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Additionally, the phrase "based on" should be interpreted to mean "based, at least in part, on."

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
receiving, by one or more computer processors, monitoring data associated with monitoring a user, wherein the monitoring data is generated by one or more sensors;
analyzing, by one or more computer processors, visual monitoring data, from the one or more sensors, related to skin associated with neck and throat areas of the monitored user utilizing image recognition, wherein analyzing visual monitoring data related to the skin associated with the neck and throat areas of the monitored user utilizing image recognition further comprises:
identifying, by one or more computer processors, one or more changes related to the skin associated with the neck and throat areas of the monitored user including a texture change and identifying an irregularity of the skin;

determining, by one or more computer processors, a state of health of the monitored user by utilizing the image recognition analyses related to the skin associated with the neck and throat areas of the monitored user utilizing a machine learning model, wherein the machine learning model is associated with the monitored user utilizing known conditions associated with the monitored user, historical medical information corresponding to the monitored user, and information associated with a known state of health corresponding to the monitored user;

determining, by one or more processors, whether the determined state of health of the monitored user corresponds to a normal state of health for the user;

in response to determining that the determined state of health of the monitored user does not correspond to the normal state of health for the user, querying, by one or more processors, the user for additional information;

determining, by one or more computer processors, a level of urgency based upon the determined state of health of the monitored user, additional information received from the user in response to the query, the monitoring data, and querying a medical database;

modifying, by one or more computer processors, the machine learning model based on the additional information received from the user in response to the query; and transmitting, by one or more computer processors, one or more respective notifications to one or more devices based, at least in part, on the determined state of health of the user and the corresponding level of urgency, wherein the one or more devices includes a device associated with the monitored user, and wherein a notification includes the determined state of health and the corresponding determined state of urgency associated with the monitored user.

2. The computer-implemented method of claim 1, further comprising:

determining, by one or more computer processors, that the machine learning model does not determine a state of health of the monitored user;

receiving, by one or more computer processors, a dictate to update the machine learning model that generated a false-positive result by obtaining feedback from the monitored user; and notifying, by one or more computer processors, the monitored user to provide feedback related to a state of health, as interpreted by the monitored user and information related to the received monitoring data.

3. The computer-implemented method of claim 1, wherein the monitoring data further includes information related to one or more physical characteristics of neck and throat areas of the monitored user, selected from the group consisting of: information associated with a skin condition, a degree of tension in one or more muscles, one or more lumps under the skin, and a physical orientation of the monitored user; and wherein the monitoring data further includes environmental factors associated with the monitored user, selected from the group consisting of: one or more items of apparel in proximity to the neck and throat areas, a temperature in proximity to the monitored user, and a level of stress associated with the monitored user.

4. The computer-implemented method of claim 1, wherein querying the user for additional information further comprises:

querying, by one or more processors, the user for information associated with a sensor of the one or more sensors; and receiving, by one or more processors, information indicating whether the sensor of the one or more sensors is operating correctly.

5. The computer-implemented method of claim 1, wherein querying the user for additional information further comprises program instructions to:

querying, by one or more processors, the user for information associated with a current medical status of the user; and receiving, by one or more processors, information indicating whether the user is currently experiencing a medical condition.

6. The computer-implemented method of claim 1, wherein the monitoring data further includes information related to one or more physical characteristics of neck and throat areas of the monitored user, including, a degree of tension in one or more muscles.

7. The computer-implemented method of claim 1, wherein the monitoring data further includes information related to one or more physical characteristics of neck and throat areas of the monitored user, including, a physical orientation of the monitored user.

8. The computer-implemented method of claim 1, wherein the monitoring data further includes environmental factors associated with the monitored user, including one or more items of apparel in proximity to the neck and throat areas.

9. The computer-implemented method of claim 1, wherein the monitoring data further includes environmental factors associated with the monitored user, including a level of stress associated with the monitored user.

10. The computer-implemented method of claim 1, wherein the visual monitoring data comprises non-visible colors.

11. The computer-implemented method of claim 1, wherein a first sensor of the one or more sensors comprises a temperature sensor embedded within a dental device, further comprising:

analyzing, by one or more computer processors, temperature data of items consumed by the monitored user; and wherein determining the state of health of the monitored user further utilizes the temperature data analysis.

* * * * *